(12) United States Patent
Doyle et al.

(10) Patent No.: US 8,995,066 B2
(45) Date of Patent: Mar. 31, 2015

(54) PASSIVE POSITION COMPENSATION OF A SPINDLE, STAGE, OR COMPONENT EXPOSED TO A HEAT LOAD

(75) Inventors: Paul Doyle, San Jose, CA (US); Alexander Belyaev, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 876 days.

(21) Appl. No.: 13/226,492

(22) Filed: Sep. 6, 2011

(65) Prior Publication Data

US 2013/0057855 A1    Mar. 7, 2013

(51) Int. Cl.
G02B 7/00    (2006.01)
G01N 21/95    (2006.01)

(52) U.S. Cl.
CPC ............ *G02B 7/008* (2013.01); *G01N 21/9501* (2013.01); *G01N 2201/021* (2013.01)
USPC .......................................................... 359/820

(58) Field of Classification Search
USPC ............................ 359/811, 819, 820; 384/278
See application file for complete search history.

(56) References Cited

U.S. PATENT DOCUMENTS

| | | | |
|---|---|---|---|
| 4,597,708 A | 7/1986 | Wheeler | |
| 4,601,576 A | 7/1986 | Galbraith | |
| 4,641,967 A | 2/1987 | Pecen | |
| 4,766,324 A | 8/1988 | Saadat | |
| 5,938,344 A * | 8/1999 | Sabin | ............................ 384/278 |
| 2008/0193201 A1 | 8/2008 | Kwan | |

FOREIGN PATENT DOCUMENTS

| | | |
|---|---|---|
| KR | 1020030050623 A | 6/2003 |
| KR | 10-2004-0052467 A | 6/2004 |
| WO | 2008029158 A2 | 3/2008 |

* cited by examiner

*Primary Examiner* — Joseph P Martinez
(74) *Attorney, Agent, or Firm* — Deborah Wenocur

(57) ABSTRACT

Disclosed herein is an apparatus for providing passive correction for thermal effects on a mounted mechanical component. Further disclosed is a wafer inspection system employing the passive thermal effect correction apparatus.

12 Claims, 3 Drawing Sheets

PASSIVE POSITION COMPENSATION OF A SPINDLE, STAGE, OR COMPONENT EXPOSED TO A HEAT LOAD

FIELD OF THE INVENTION

This invention pertains to thermal effects, and in particular to passive compensation for thermal effects on components exposed to a heat load.

BACKGROUND

Thermal effects are ubiquitous, and have great effects on many systems. Thermal expansion, and in addition differences in coefficients of thermal expansion (CTE"s) between components, can lead to errors and other problems. An example is a spindle in a wafer inspection system. Due to the high wafer rotation speed and therefore high spindle power, there is a large resulting heat rise during wafer inspection. Any change in temperature affects the position of a component such as the spindle, due in part to the mounting materials' CTE. This change in position can degrade inspection accuracy and sensitivity. For example, for an aluminum system, given the size of the spindle and the CTE of aluminum, a 2 degrees C. temperature shift can result in XY accuracy out of spec. Similar thermal effects can have negative impact on many other mechanical systems such as machine tools. Attempts have been made to minimize thermal displacement by using materials with a very low CTE such as Invar, a nickel steel alloy notable for its uniquely low coefficient of thermal expansion. However, use of such materials as Invar creates new problems. If a portion of the system is Invar, with a CTE approximately zero, and the rest of the system is aluminum with a CTE of 24 um/m/° C., this creates a sensitivity to environmental temperature change. And Invar is prohibitively expensive to use for serious structural work. Keeping everything aluminum eliminates this problem.

Some efforts have been made to correct for thermally-induced errors on machine tools via software. No such corrections have been implemented for wafer inspection systems such as Surfscan from KLA-Tencor. As customer requirements have driven wafer inspection throughput requirements to higher levels, the necessary increase in spindle power has resulted in an increased heat load, to the point that correction of thermal effects has become very important for maintaining defect location accuracy.

SUMMARY OF THE INVENTION

Disclosed herein is an apparatus for providing passive correction for thermal effects on a mounted mechanical component. Further disclosed is a wafer inspection system employing the passive thermal effect correction apparatus.

DETAILED DESCRIPTION

The invention will be illustrated with an embodiment directed to a wafer inspection system, and in particular the wafer mount spindle. However, note that the inventive concept and a similar apparatus can be utilized for many other applications including but not limited to: metrology, measurement, data writing and reading, and microscope systems.

Referring to the wafer inspection system embodiment, current methods result in errors in defect location accuracy. Even if some software correction of defect location based on temperature were used, relatively large errors can result during temperature transients as the machine warms up or cools down. Disclosed hereinafter is a completely passive control over temperature related spindle position errors which reduces defect location error from up to about 50 microns to less than 5 microns. And this smaller error can be further reduced using software correction. As the overall magnitude of error is greatly reduced, further software correction will be much more accurate, especially during transient states.

In an embodiment of the invention, position change of a component is corrected passively by mounting the component on unequal length elements such that the temperature distribution across the mounting elements combines with the physical configuration to cancel out movement due to thermal expansion of the mounting elements.

Figure 1A:
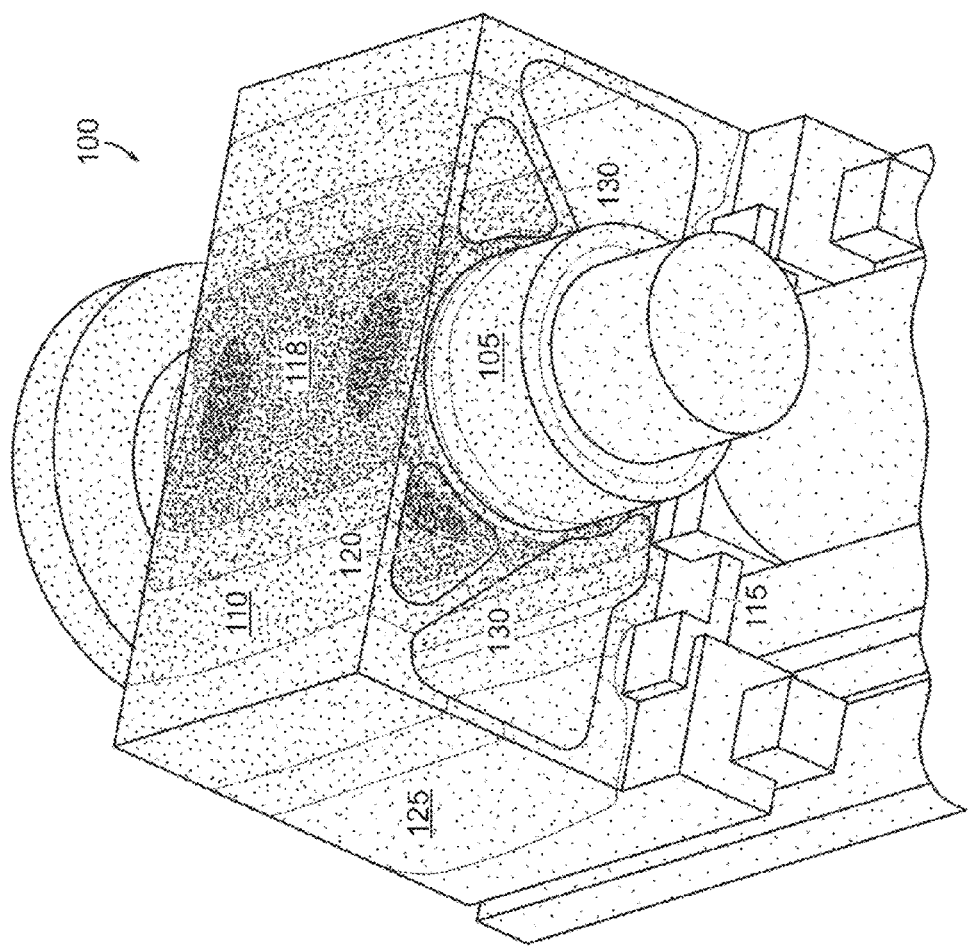
FIG. 1a shows the mounting of a spindle on a system such as a wafer inspection system.
Figure 1A:
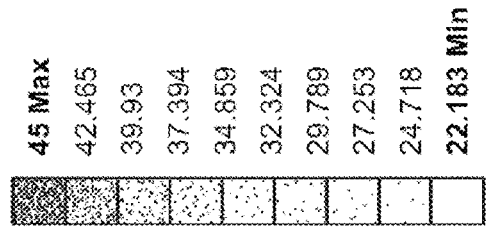
Figure 1B:
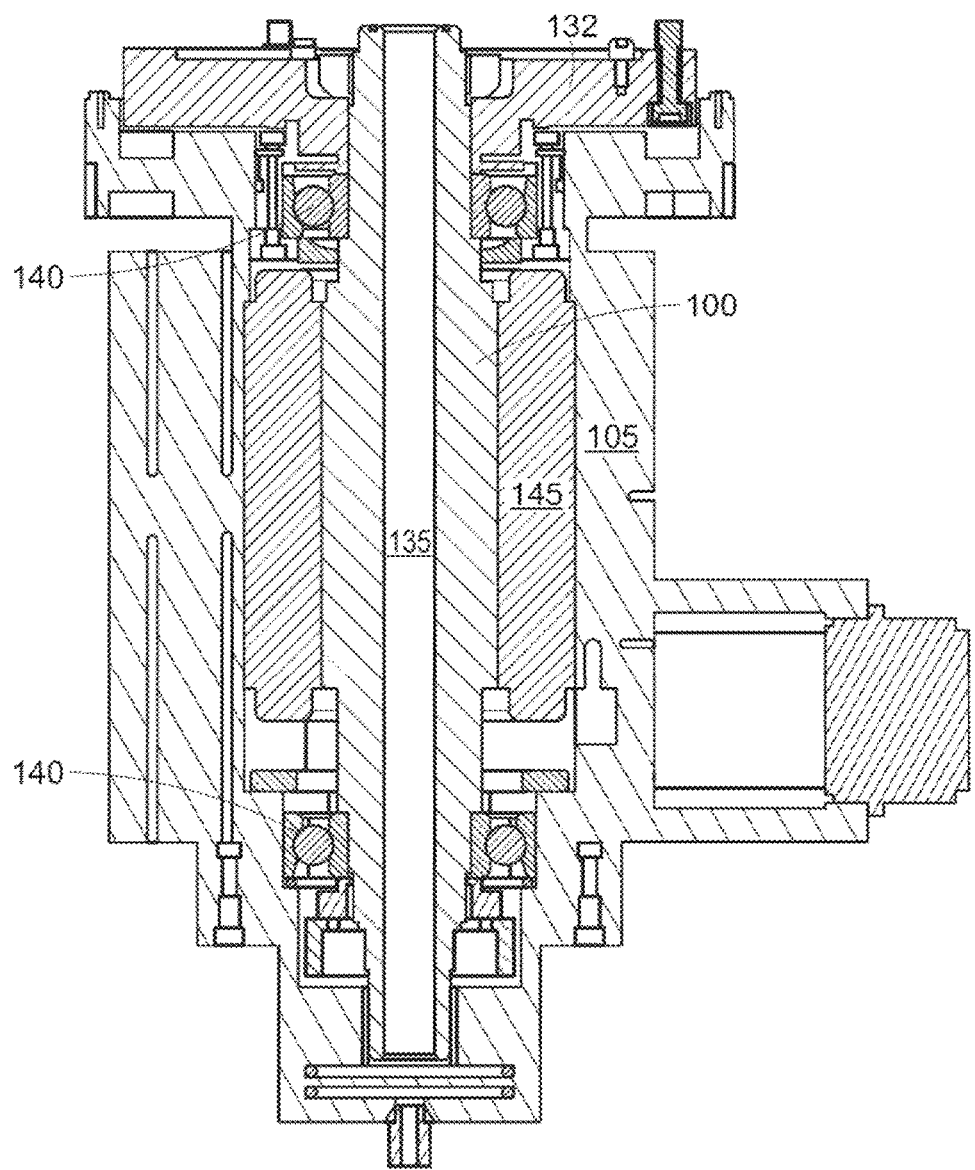
FIG. 1b shows a cutaway view of a cross section of the spindle assembly within the spindle housing.

FIG. 1a shows an embodiment of the mounting of a spindle on a system such as a wafer inspection system. Spindle assembly 100 is housed within spindle housing 105. FIG. 1b shows a cutaway view of a cross section of the spindle assembly 100 within spindle housing 105. Platen 132 (also termed "spindle flange") is mounted on spindle rotor 135. Spindle bearings 140 facilitate spindle rotation. Spindle motor 145 powers spindle rotation, and is the major heat source. Spindle housing 105 is connected to outer housing 110 which is attached to mechanical mounting plane 115. The outer housing 110 is constructed from a series of elements which conduct heat away from spindle motor. These elements each have a temperature gradient across them with the hottest end nearest the spindle motor 145 and the coolest end near mechanical ground, which in this case is the mechanical mounting plane 115. As will be shown hereinafter, the construction is such that the hotter and shorter inner elements cause the spindle to move in one direction, and the cooler and longer outer elements cause the spindle to move in the opposite direction an equal amount. With the proper geometry for a given heat load and available convection cooling, these effects cancel each other, resulting in no movement of the spindle. Even with varying heat load and some transient effects it is possible to reduce the error to several microns. A non-compensated spindle of similar design and power would show thermal drift on the order of 50 microns. The temperature distribution is shown. Note that the temperature is higher in regions 118 and 120 near spindle motor 145, and is lower at side walls 125 further removed from spindle motor 145. In addition to central region 118, diagonal mounting arms 130 are also hotter than side walls 125.

Figure 2:
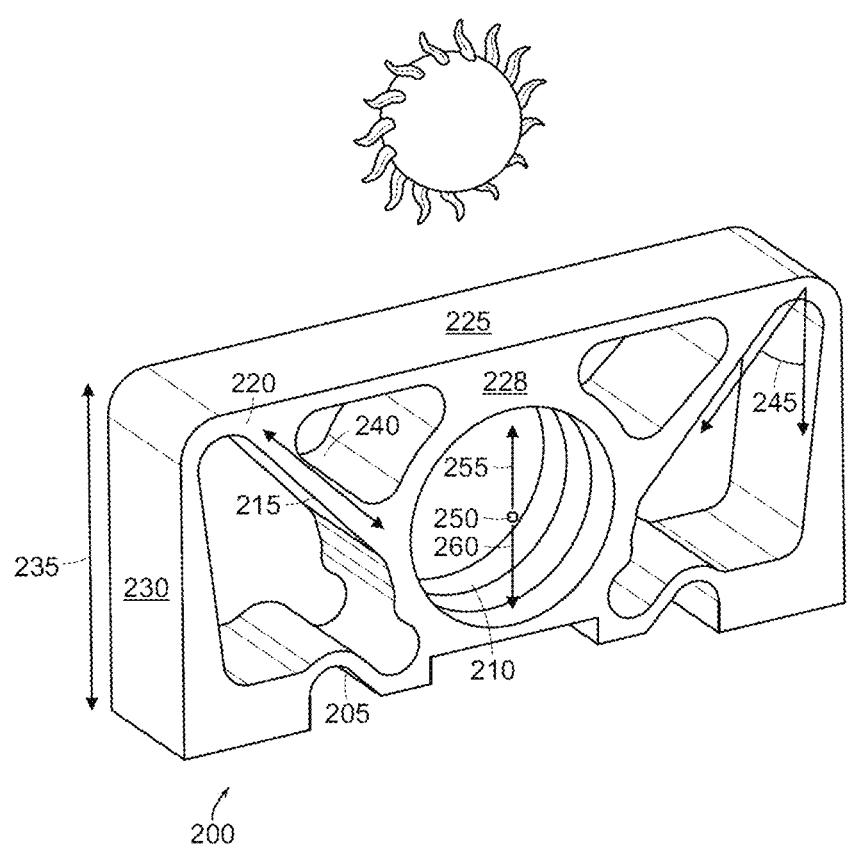
FIG. 2 shows the geometry of the outer housing 110, which is used to illustrate how the thermal position compensation works.

FIG. 2 shows the geometry of an embodiment of the outer housing 110, which is used to illustrate how the thermal position compensation works. Bottom corner edges 200 are fixedly attached to mechanical mounting plane 115. Flexible elements 205 are positioned between bottom corner edges 200. The flexible element or elements allows the design to work over a wide temperature range, and allow the housing to change size with thermal load, while minimizing the distortion of the rest of the system it is mounted to. Spindle 100 (and spindle motor 145) located in orifice 210 acts as a localized heat source when rotating. Diagonal mounting arms 215 are attached to front wall 220, which is free standing at outer surface 225. Spindle 100 is attached directly to front wall 220 by thick region 228. Side walls 230 are fixed to bottom corner edges 200. Assume side walls 230 have length L1 (235), and that diagonal mounting arms 215 have length L2 (240), and are mounted at angle θ (245) from side walls 230. To present a simplified description of the effect, we will assume that each element has a well defined temperature across its length. (In reality, the temperature distribution will be more complex, with temperature gradients across the elements). Assume a temperature change ΔT. Then each component of length L will change its length by $\Delta L = L\alpha\Delta T$, where $\alpha = CTE$, the coefficient of thermal expansion. In particular, the sidewall lengths will change by $\Delta L1 = L1\alpha\Delta T1$ and the diagonal mounting arm lengths will change by $\Delta L2 = L2\alpha\Delta T2$, where ΔT1 and ΔT2 are the temperature changes for the sidewall and diagonal mounting arms, respectively. The expansion of the side walls will cause displacement X1=ΔL1 of center 250 of spindle 100 in upward direction 255 (which will be defined as the positive direction). However, the expansion of the diagonal mounting arms will cause displacement X2 approximately equal to ΔL2 sin θ of center 250 of spindle 100 in downward direction 260 (which will be defined as the negative direction). Expansion of thick region 228 will cause displacement X3 in the downward, i.e. negative, direction. (Note again that this description is simplified but indicates the key components of expansion which cause movement of the spindle in opposing directions). Flexible elements 205 allow for movement of the spindle according to the above mentioned expansions. Because of the opposing movements due to the side walls 230 in the positive direction, and the diagonal mounting arms 215 and thick region 228 in the negative direction, the movements can be designed to cancel each other out if the lengths and angles are properly chosen according to the relative temperature changes in the two elements. In particular:

Displacement=0 if $X1+X2+X3=0$.

Determination of element lengths has been simulated using a multiphysics FEA (Finite Element Analysis) program which provides modeling of simultaneous effects of: the heat load of the spindle motor, the convective cooling of air, and the thermal displacement of the housing. This may alternatively be done in an iterative fashion with conventional FEA, or possibly with manual calculations for simple systems, but these alternative methods would be much more time consuming.

The inventive concept of this design may also be used to correct for a heat load external to the component, effectively isolating the component from warm devices mounted near the component of interest.

The inventive concept of this design can be used for passive position correction of a positioning stage due to thermally induced error in systems including but not limited to: inspection (including bare wafer inspection, patterned wafer inspection, LED inspection, solar PV cell inspection, disk drive inspection, optical media inspection), metrology including wafer metrology, measurement, data writing and reading, microscope systems, voice coil motors, linear motors, semiconductor manufacturing tools, machine tools, high accuracy robotics, amplifiers, optical components, sensors, DNA sequencing, chemical analysis, and power supplies. It can also be used for passive position correction for thermally induced error in the above cited systems. This concept can be used in a similar manner to cancel thermal drift of optical components or sensors exposed to heat loads. Heat loads can be internal as in the case of the spindle disclosed herein, or the concept can be reversed to compensate for an external heat source such as a motor or electronic component mounted nearby. FIG. 2 is further illustrative of using the inventive method and apparatus to isolate an element such as an optical element, or a sensor such as a CCD or position sensing device, from an external heat source (represented by the sun in the figure).

Note that the thermal compensation apparatus and method disclosed herein is applicable in the temperature range where structural deformation, e.g. thermal expansion, depends linearly on temperature variation. This large but limited temperature interval encompasses the temperature ranges encountered by the spindle of a wafer inspection system as described herein.

An additional benefit from use of the inventive design is: Often it is desirable to maintain a substantially constant CTE in a system, i.e., to utilize similar surrounding materials such as aluminum, so that all components share the expansion rate with surrounding components for a change in environmental temperature. Use of the inventive design allows use of materials such as aluminum while still compensating for a localized heat gradient. This can prove to be a better solution than using expensive materials such as Invar which may work well for reducing drift due to thermal gradients, but can cause errors with respect to surrounding components when environmental temperature changes. In particular, the inventive design enables maintaining the plane position of a component mounted within a system regardless of temperature, while still maintaining the out of plane CTE of the system. For example, if an optical element was mounted using the inventive design to a device in an aluminum structure that supported other optical elements, then a nearby heat source such as an illumination lamp would not cause the optical element to deviate off the optical axis. Because the device is made of aluminum and the main optical structure is also made of aluminum, the common CTE would normalize any out of plane displacement with respect of the rest of the system, due to the matched CTE. This solution would not be possible using a zero CTE material such as Invar in an aluminum system.

In the application of the spindle of a wafer inspection system, defect location accuracy is of primary importance, as is maximizing throughput. Higher throughput requires higher spin rates and acceleration, which increases the amount of heat generation. Uncorrected, this heat inevitably leads to increased errors in defect location.

Between the previous generation of the Surfscan wafer inspection system and the current generation, the power dissipated in the spindle during inspection has more than doubled, as has the corresponding heat load. Despite the large increase in heat load, with use of the spindle mounting design disclosed herein the overall accuracy has greatly improved.

It is not expected that the invention be restricted to the exact embodiments disclosed herein. Those skilled in the art will recognize that changes and modifications can be made without departing from the inventive concept. By way of example, the configuration of the mounting elements need not be exactly as shown. Other configurations may be designed that result in opposing motions due to thermal expansion, which cancel each other out. The scope of the invention should be construed in view of the claims.

With this in mind, we claim:

1. An apparatus for providing passive correction for thermal effects on a mechanical component mounted on a system comprising:
   a physical configuration for mounting said mechanical component on said system, said physical configuration designed to result in opposing motions of said mechanical component relative to said system, due to thermal expansion;

said opposing motions substantially canceling each other out for a thermal range where thermal expansion depends linearly on temperature variation;

wherein said mechanical component is substantially stationary relative to said system during temperature variation within said thermal range.

2. The apparatus of claim 1, wherein said physical configuration comprises unequal length mounting elements designed such that temperature distribution across the mounting elements combines with the physical configuration to cancel out movement due to thermal expansion of the mounting elements.

3. The apparatus of claim 2, wherein said unequal length mounting elements include:

a first set of mounting elements having a first length;

a second set of mounting elements having a second length shorter than said first length;

said second set of mounting elements undergoing greater temperature variation than said first set of mounting elements;

said first set of mounting elements causing motion of said mechanical component in a first direction; and said second set of mounting elements causing motion of said mechanical component in a second direction opposite said first direction.

4. The apparatus of claim 3, wherein said mechanical component is one of: an optical element, a sensor, a Charge Coupled Device (CCD), and a position sensing device; and wherein said mechanical component is in proximity to a heat source.

5. The apparatus of claim 3 wherein temperature is lower for mounting elements at greater distance from said mechanical component.

6. The apparatus of claim 5 including a heat source proximal said mechanical component.

7. The apparatus of claim 5 including a heat source external to said system.

8. The apparatus of claim 1, wherein said system is a wafer inspection system and said mechanical component is a spindle.

9. The apparatus of claim 1, wherein said system is an LED inspection system and said mechanical component is a spindle.

10. The apparatus of claim 1, wherein said system is a hard disk drive inspection system and said mechanical component is a spindle.

11. The apparatus of claim 1, wherein said system is an optical media inspection system and said mechanical component is a spindle.

12. A wafer inspection system including a spindle mounted thereto with the apparatus of claim 1.

* * * * *